(12) United States Patent
Revivo

(10) Patent No.: US 7,318,828 B1
(45) Date of Patent: Jan. 15, 2008

(54) MICRODERMABRASION MACHINE

(76) Inventor: Jacob Revivo, 14936 Camarillo St., Sherman Oaks, CA (US) 91403

( * ) Notice: Subject to any disclaimer, the term of this patent is extended or adjusted under 35 U.S.C. 154(b) by 645 days.

(21) Appl. No.: 10/945,584

(22) Filed: Sep. 20, 2004

(51) Int. Cl.
 *A61B 17/50* (2006.01)
(52) U.S. Cl. ........................................ 606/131
(58) Field of Classification Search ................ 606/131, 606/132, 133, 127, 128; 604/289, 290; 451/87, 451/88
See application file for complete search history.

(56) References Cited

U.S. PATENT DOCUMENTS

| | | | |
|---|---|---|---|
| 6,241,739 B1 | 6/2001 | Waldron | |
| 6,423,078 B1 | 7/2002 | Bays | |
| 6,500,183 B1 | 12/2002 | Waldron | |
| 6,527,783 B1 * | 3/2003 | Ignon | 606/131 |
| 6,582,442 B2 | 6/2003 | Simon | |
| 6,629,983 B1 | 10/2003 | Ignon | |
| 6,641,591 B1 | 11/2003 | Shadduck | |
| 6,695,853 B2 | 2/2004 | Karasiuk | |

* cited by examiner

*Primary Examiner*—Kevin T. Truong
(74) *Attorney, Agent, or Firm*—Thomas I. Rozsa

(57) ABSTRACT

An improved microdermabrasion machine which uses a combination of powdered crystals which is sprayed onto the surface of the skin combined with an exfoliating head which rubs the crystals against the skin to exfoliate dead skin, combined with a suction device to remove the powdered crystals after they have performed their exfoliating process.

18 Claims, 4 Drawing Sheets

MICRODERMABRASION MACHINE

BACKGROUND OF THE INVENTION

1. Field of the Invention

The present invention relates to a machine to treat human skin. Specifically, the field of the invention relates to machines which are used to exfoliate dead layers of skin through the use of abrasive materials combined with a suction to remove the abrasive materials after they have been used to abrade dead skin cells.

2. Description of the Prior Art

There are many machines in the field of microdermabrasion machines that have been in existence for a period of time. The inventor is aware of U.S. Pat. No. 6,500,183 B1 issued on Dec. 31, 2002 to Stephen H. Waldron and assigned to Altair Instruments, Inc. for Microdermabrasion Device (hereafter "'183 Patent"). The fundamental principle of the '183 patent is to include within the hand piece a rotatable abrasive pad which is used in the microdermabrasion process to abrade the dead skin cells. It is believed that this involves a device which can be more harmful to the skin than beneficial.

The following patents are relevant to the present invention:

1. U.S. patent application Publication No. 2001/0023351 A1 to Eilers on Sep. 20, 2001 for "Skin Abrasion System And Method" (hereafter the "Eilers Patent Application");

2. U.S. Pat. No. 6,423,078 B1 issued to Bays on Jul. 23, 2002 for "Dermabrasion Instrument, Instrument Assembly And Method" (hereafter the "Bays Patent");

3. U.S. patent application Publication No. 2002/0151908 A1 to Mallett on Oct. 17, 2002 for "Microdermabrasion And Suction Massage Apparatus And Method" (hereafter the "Mallett Patent Application");

4. U.S. patent application Publication No. 2002/0169461 A1 to Simon on Nov. 14, 2002 for "Method And System For Performing Microabrasion" (hereafter the "Simon Patent Application");

5. U.S. Pat. No. 6,500,183 B1 issued to Waldron on Dec. 31, 2002 for "Microdermabrasion Device" (hereafter the "'183 Waldron Patent");

6. U.S. patent application Publication No. 2003/0060834 A1 to Muldner on Mar. 27, 2003 for "Single-Hand Operable Microdermabrasion Device" (hereafter the "Muldner Patent Application");

7. U.S. Pat. No. 6,582,442 B2 issued to Simon on Jun. 24, 2003 for "Method And System For Performing Microabrasion" (hereafter the "Simon Patent");

8. U.S. Pat. No. 6,629,983 B1 issued to Ignon on Oct. 7, 2003 for "Apparatus And Method For Skin/Surface Abrasion" (hereafter the "Ignon Patent");

9. U.S. Pat. No. 6,641,591 B1 issued to Shadduck on Nov. 4, 2003 for "Instruments And Techniques For Controlled Removal Of Epidermal Layers" (hereafter the "Shadduck Patent");

10. U.S. Pat. No. 6,695,853 B2 issued to Karasiuk on Feb. 24, 2004 for "Microdermabrasion System And Method Of Use" (hereafter the "Karasiuk Patent");

11. U.S. Pat. No. 6,241,739 B1 issued to Waldron on Jun. 5, 2001 for "MICRODERMABRASION DEVICE AND METHOD OF TREATING THE SKIN SURFACE" (hereafter the "'739 Waldron Patent").

The Eilers Patent Publication relates to a skin abrasion system and method. The focus is that rounded particles may be used as an abrasive during a microdermabrasion procedure. Rounded particles may be propelled against the skin within a treatment area to treat the skin. The focus of the invention is to propel a combination of either rounded particles and other abrasives such as sharp edge particles. The sharp edge particles may be glass, sand, aluminum oxide etc. The machines has a dispensing tip to dispense the rounded particles.

The Bays Patent is a dermabrasion instrument 12 which includes an outer member 16 which is held stationary by the handpick 14 and an inner member 18 which is disposed at least partly within the outer member and rotated by the hand piece. It is also shielded by a portion of the tubing 28. It does not disclose the concept of spraying onto the skin fine particles combined with an abrading tip.

The Mallett Patent Application includes the combination of a microdermabrasion and suction massage apparatus in a single unit. The microdermabrasion section of the unit includes a crystal pickup station operating with a venturi effect to draw crystals through a hole into an air stream. The step is followed by performing a suction massage procedure at the operative site in order to promote the healing of the abraded skin. A first air stream is directed through a source of crystals which are introduced into the first air stream to provide a flow of crystals which is then sent to the microdermabrasion hand piece. This discloses the concept of the microdermabrasion machine having crystals sprayed onto the skin but does not have the combination of an abrading exfoliating tip.

The Simon Patent Application discloses a method and system for performing microdermabrasion. This is another patent application which discloses a variation on the concept of spraying abrading crystals onto the skin through a microdermabrasion machine. Once again, this does not disclose the concept of having an abrasive tip in combination with spraying the crystals thereon.

The Muldner Patent Application discloses a single hand operable microdermabrasion device. This once again discloses an abrading device having an abrading surface but does not disclose the concept of using it in combination with the sprayed on particles.

The Simon Patent is a method and system for performing microabrasion. It discloses a dermabrasion apparatus for delivering and retrieving material to and from the portion of the skin to be abraded and a delivery and retrieval hand piece and an abrasive handling device, and a waste retrieval device. It has certain features including a funnel shaped delivery chamber. This does not disclose the concept of an abrasive tip in combination with the spray on crystals.

The Ignon Patent discloses an apparatus and method for skin surface abrasion. This once again discloses a variation of having a microdermabrasion tool with an abrasive front section but does not disclose the concept of combining this abrasive tip with the spray-on crystals.

The Shadduck Patent discloses an instrument for controlled removal of epidermal layers. In this case the patent discloses a handheld instrument having a vacuum aspiration system, a source to deliver sterile fluids or pharmacological agents onto the skin, and a skin interface surface in the end that has a special shape for abrading the layers of the skin as the end is moved over the patient's skin while at the same time causing rapid penetration of the fluids into the skin.

The Karasiuk Patent discloses an applicator tool with a non-abrasive tip with one opening therethrough and an abrasive member located internally of the applicator tool and means for applying a vacuum so that a portion of the skin is drawn into contact with the abrasive member and abraded.

The '183 Waldron Patent requires the use of a rotatable abrasive pad to remove dead skin cells which may be more harmful than beneficial to the skin.

The '739 Waldron Patent has an abrasive tip which is supported on a connector tube or lumen which in turn is connected to a line connected to a source of vacuum.

The present invention seeks to improve upon the field of microdermabrasion machines by not having an abrasive wheel but instead, having an improved abrasive element to facilitate the skin exfoliation process.

SUMMARY OF THE INVENTION

The present invention is an improved microdermabrasion machine which uses a combination of powdered crystals which is vacuum sprayed onto the surface of the skin combined with an exfoliating head which rubs the crystals against the skin to exfoliate dead skin, combined with a suction device to remove the powdered crystals after they have performed their exfoliating process.

It has been discovered, according to the present invention, that if a combination of powdered crystals is sprayed onto the skin and abraded against the dead skin with an exfoliating tip made of an exfoliating material, and is thereafter removed by suction, it has a very fine cosmetic effect to improve the skin surface by removing dead skin cells and other unsightly skin blemishes such as crows feet and wrinkle lines.

It is therefore an object of the present invention to provide an improved microdermabrasion machine which has beneficial effects over the prior art to create an improved exfoliating skin effect.

Further novel features and other objects of the present invention will become apparent from the following detailed description, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
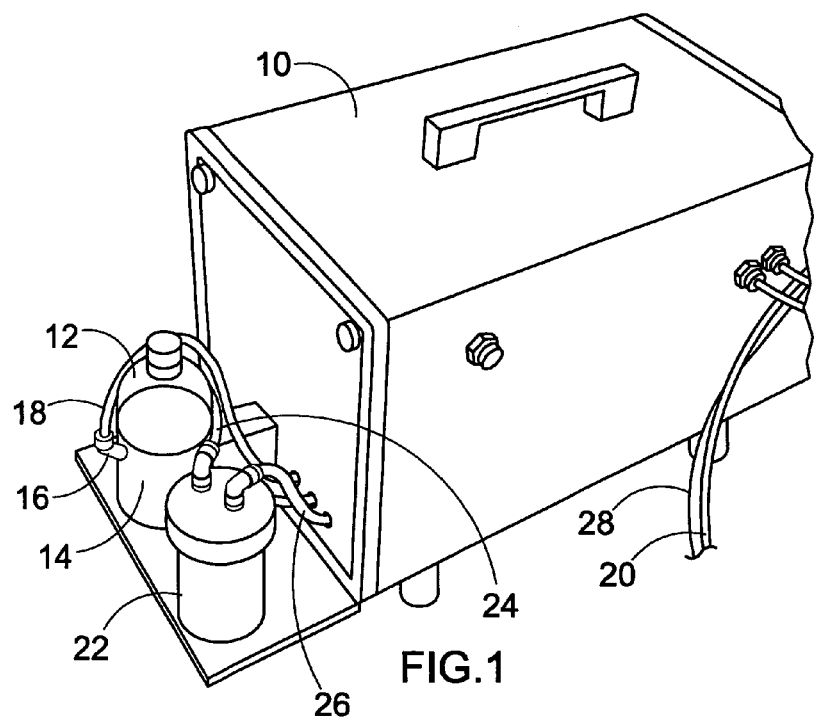
FIG. 1 is a perspective view of the present invention improved microdermabrasion machine showing the container housing powdered crystals and an empty container to receive used powdered crystals, and the lines leading to each container.

Referring to FIG. 1, the present invention microdermabrasion machine is disclosed. Specifically, the present invention microdermabrasion machine 10 consists of a suction pump which is connected to external jars. Specifically, there is a first external jar 12 which contains within it the powdered crystals 14. At the bottom of the jar is a connector member 16 which leads to a first tube 18. The first tube 18 is connected to the suction device within the machine 10 and leads to a discharge tube 20 which is connected to the hand piece. When activated, the powdered crystals are sucked out of the jar 12, travel through tube 18, travel through tube 20 to the hand piece and are discharged from the hand piece. Also shown in FIG. 1 is a receptacle jar 22. The receptacle jar 22 contains receipt lines 24 and 26. The lines extend into a suction device within the machine 10 and then extend out to line 28. Line 28 also leads to the hand piece.

Figure 2:
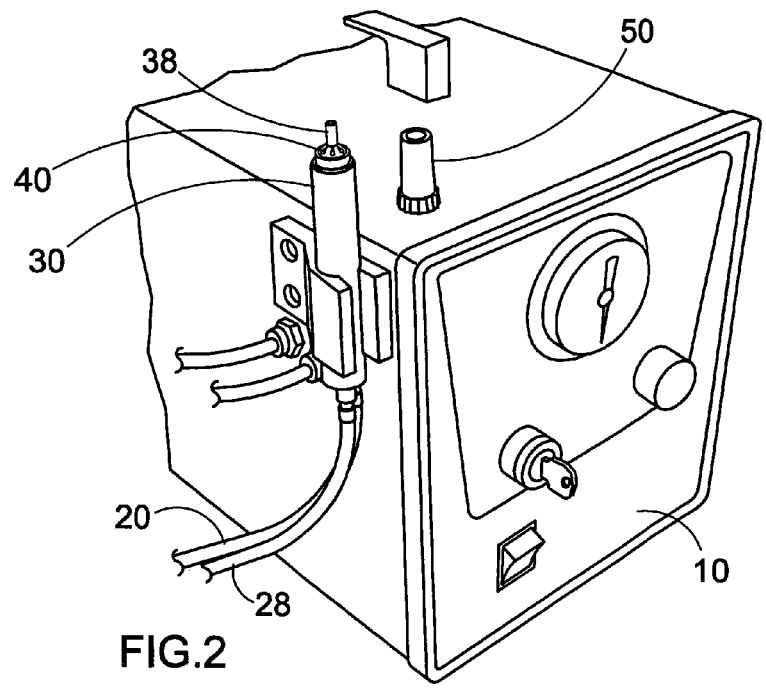
FIG. 2 is another perspective view of the present invention improved microdermabrasion machine showing the hand piece with the abrasive cap removed and the lines leading from the powdered crystal container and the used powdered crystal container leading to the hand piece.

Referring to FIG. 2, the hand piece 30 is shown. Also shown is suction delivery line 20 which receives the powdered crystals from receptacle 12 and the suction line 28 which creates a suction through which the powdered crystals 14 are retrieved.

Figure 3:
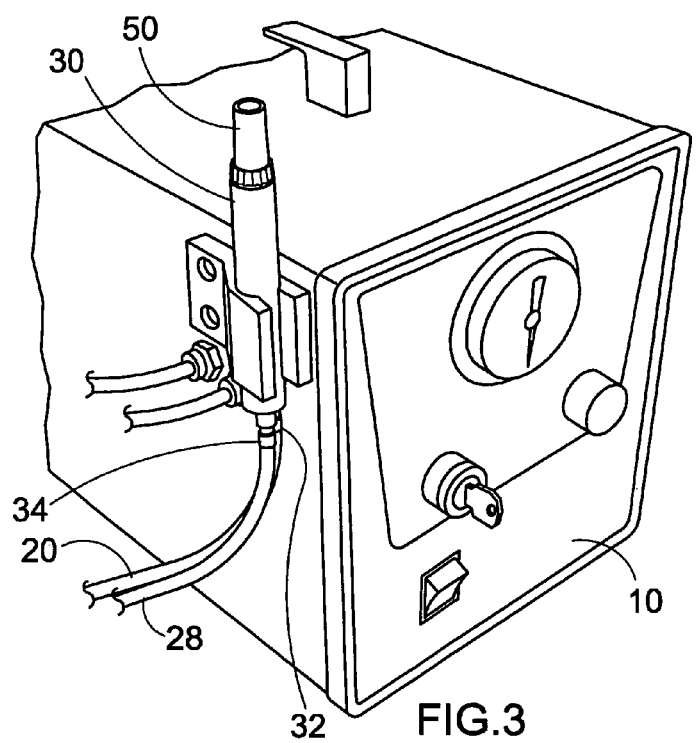
FIG. 3 is another perspective view of the improved microdermabrasion machine showing the hand piece with the abrasive cap inserted at the end of the hand piece and also showing the lines from the powdered crystals container and the used powdered crystals container leading to the hand piece.
Figure 4:
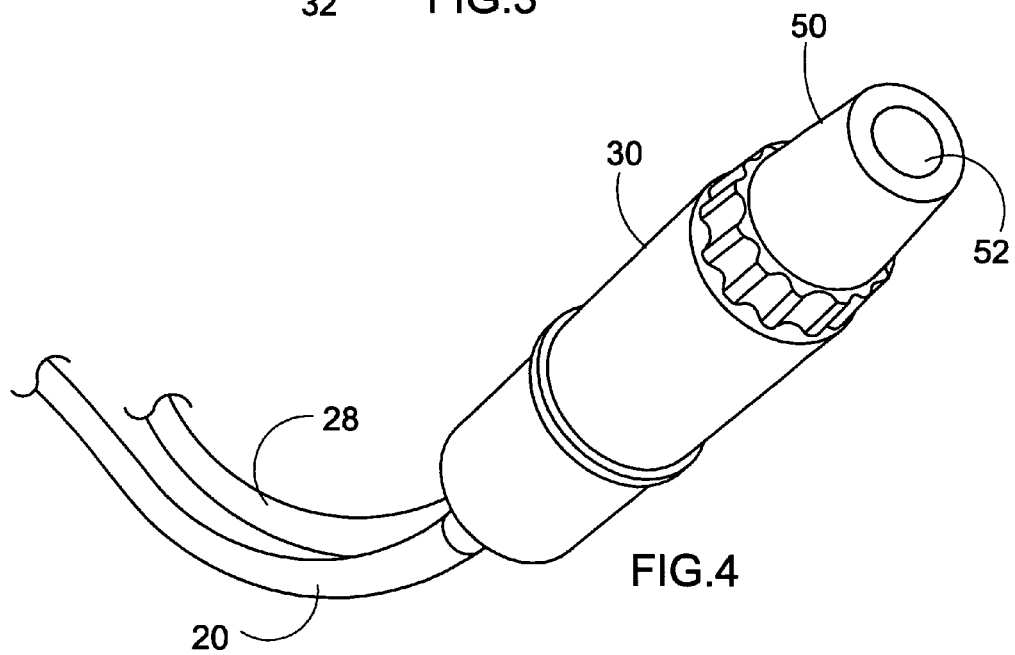
FIG. 4 is a perspective view of the hand piece showing the abrasive cap in place and the two lines leading from the hand piece to the powdered crystal reservoir and the used powdered crystal container.
Figure 5:
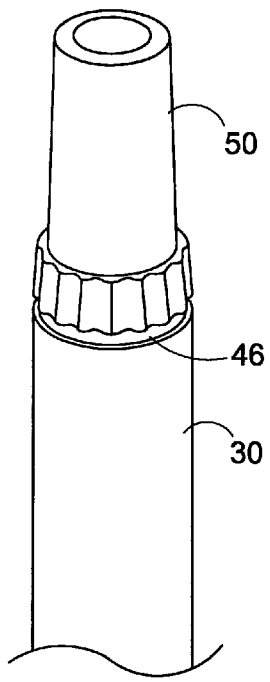
FIG. 5 is closeup perspective view of the hand piece with the abrasive cap in place.
Figure 6:
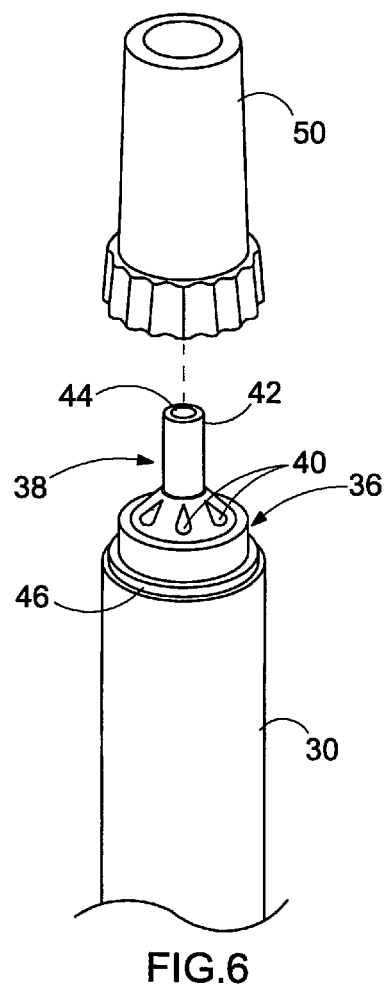
FIG. 6 is a perspective view of the hand piece showing the abrasive cap removed with the tip of the hand piece showing the central opening for powdered crystals to be vacuum blown out of the hand piece and the surrounding openings in a circle to form a suction area to remove powdered crystals.
Figure 7:
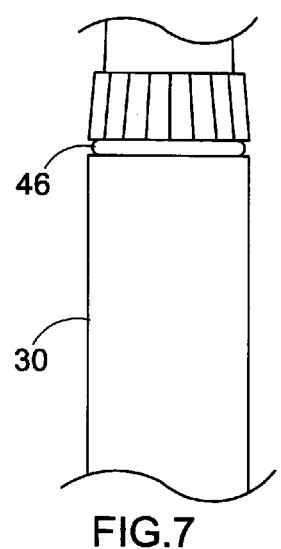
FIG. 7 is a perspective view of the hand piece showing a sealing O-ring between the abrasive cap and the body of the hand piece.
Figure 8:
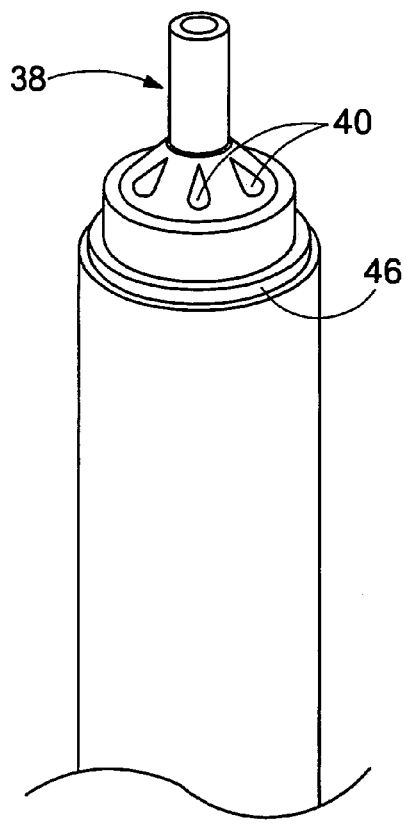
FIG. 8 is a perspective view of the hand piece of the present invention with the cap removed and showing the sealing O-ring in greater detail.

Referring to FIGS. 3 through 7, the hand piece is disclosed. Specifically, the hand piece 30 consists of a pair of receiving threaded members 32 and 34. Member 32 receives line 20 and member 34 receives line 28. At the front portion 36 of the hand piece 30 is a tip member 38. Tip member 38 comprises a suction member 42 which has an opening 44. Line 20 is connected to openings 44 so that powdered crystals 14 which are sucked from jar 12 are expelled through openings 44. Also shown is a multiplicity of openings 40. At the lower rim of the tip area is a sealing gasket 46. A key novel feature of the present invention is the inclusion of an abrasive cap 50. The abrasive cap 50 fits over the tip section 36 of the hand piece 30 as illustrated in FIGS. 3 and 5. The cap is shown removed in FIG. 6. As shown in FIG. 4, the cap has an opening 52 through which the powdered crystals 14 are expelled and through which the used powdered crystals 14 can be sucked in and returned to the reservoir jar 22.

The key innovative feature of the present invention is that the abrasive cap 50 can be made of exfoliating material. By way of example, the abrasive cap can be made from aluminum oxide, metal powder, diamond powder, lava powder and ceramic powder. These are only some examples of elements from which the abrasive cap can be made. The concept is that when the machine is turned on, the powdered crystals 14 are sucked through line 18 and extend through line 20, and extend into the hand piece 30 and are expelled from opening 44 and go through opening 52 in the abrasive cap 50 and onto the skin. Thereafter, the abrasive cap 50 is used in conjunction with the powdered crystals 14 so that the abrasive cap 50 is gently rubbed on the skin so that the powdered crystals 14 can remove dead skin. After this process is completed, the suction from the machine now causes the used powdered crystals 14, used abrasive material from cap 50 and dead skin to be sucked back through opening 52 in the abrasive cap 50, through openings 40 in the hand piece 30, through line 28 and then through lines 24 and 26 and into used crystal receptacle jar 22.

The suction effect is created as follows. When the hand piece 30 and the tip of the abrasive cap 50 are placed against the skin, the closing of opening 52 against the skin causes the vacuum to expel the powdered crystals 14 through openings 44 and 52. After the abrasive process is completed, the abrasive cap 50 is lifted slightly away from the skin so that the natural vacuum causes the used powdered crystals 14 and the dead skin to be sucked through openings 52 and 40.

Figure 9:
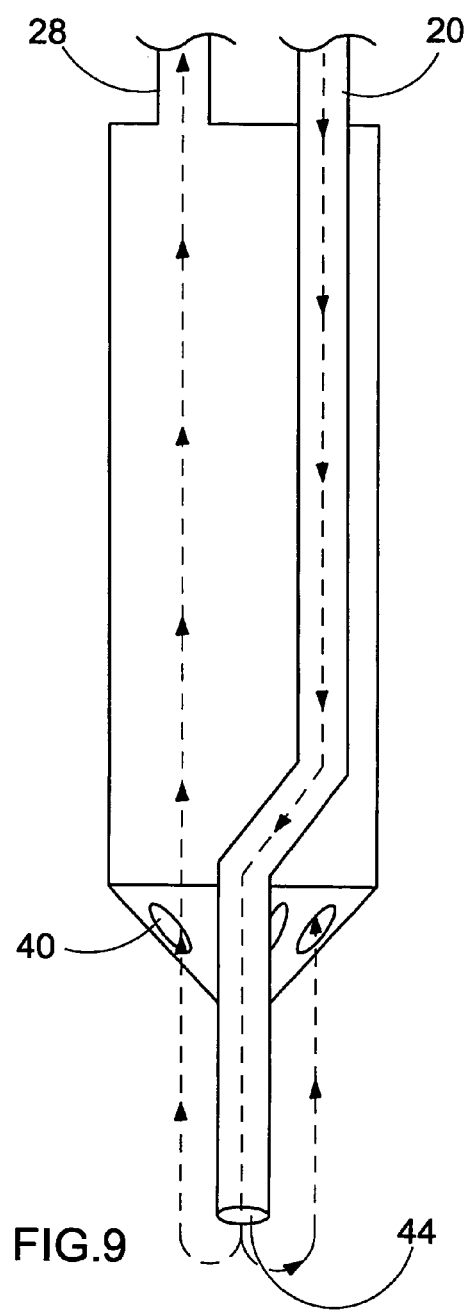
FIG. 9 is a cross-sectional view of the hand piece and suction lines to illustrate the flow of suction in the hand piece.

The suction flow is illustrated in FIG. 9. When the machine 10 is turned on so that the suction pump is operating, the suction draws the powdered crystals 14 out of jar 12 and through the delivery lines as previously discussed and to delivery line 20 which extends into hand piece 30 to hollow tip 36 so that the powdered crystals 14 are expelled through opening 44. The continuous vacuum also causes the used powdered crystals 14 and dead skin to be sucked back into opening 52 in abrasive cap 50 and then through the multiplicity of openings 40. Since the hand piece has a hollow interior, the used powdered crystals 14 and dead skin are drawn by suction to return line 28 which then returns the used powdered crystals 14 and dead skin to jar 22. The flow of arrows in FIG. 9 shows the suction airflow as just described.

Therefore, the key novel feature of the present invention is to use a combination of powdered crystals 14 which can be discharged onto the surface of the skin combined with an abrasive cap 50 which can be made of materials including, but not limited to, aluminum oxide, metal powder, diamond powder, lava powder and ceramic powder and which abrasive cap can be gently rubbed back and forth against the skin so that the powdered crystals 14 abrade the dead skin cells and thereafter the machine has a second suction device to suck the used powdered crystals and dead skin cells away from the skin, therefore leaving an undersurface of clean new skin which has now had blemishes, wrinkles, acne and other skin problems removed. The present invention creates a beautifying effect for the skin and a beautifying effect for enabling resurfacing of the skin without the use of caustic chemicals and without the use of caustic peeling chemicals which can create discoloration of the skin and also without the necessity of a tool that can substantially damage the skin such as a rotating disk.

Defined in detail, the present invention is a machine to abrade dead skin cells, comprising: (a) a first receptacle containing unused powdered crystals therein and a second receptacle to receive and retain used powdered crystals, used abrasive material and dead skin cells; (b) a suction device; (c) a hand piece comprising a first end having a first opening leading to a suction member located at a second end of the hand piece, the suction member having a central opening, the hand piece further comprising a multiplicity of second openings adjacent its second end, the multiplicity of second openings leading to an internal chamber within the hand piece which internal chamber opens into a second opening at the first end of the hand piece; (d) an abrasive cap made out of exfoliating material, the abrasive cap positioned over and surrounding the suction member, the abrasive cap having a central opening aligned with the central opening of the suction member; (e) a first delivery line connecting the first receptacle to the suction device and a second delivery line connecting the suction device to the first opening at the first end of the hand piece, so that once the suction device is turned on, the unused powdered crystals are sucked through the first delivery line and thereafter are caused to travel through the second delivery line to the hand piece; and (f) a first return line connecting the second receptacle to the suction device and a second return line connecting the suction device to the second opening at the first end of the hand piece; (g) whereby, when the suction device is turned on, the unused powdered crystals are transmitted from the first receptacle to the first opening at the first end of the hand piece and further caused to travel to the suction member from which the powdered crystals are expelled out of the central opening in the suction member and the aligned central opening in the abrasive cap and onto the surface of skin while concurrently the abrasive cap is gently rubbed on the skin so that the combination of powdered crystals and abrasive material from the abrasive cap removes dead skin cells, and thereafter the used powdered crystals, used abrasive material and dead skin cells are sucked through the multiplicity of second openings adjacent the second end of the hand piece and are sucked through the second return line, the first return line and into the second receptacle.

Defined broadly, the present invention is a machine to abrade dead skin cells, comprising: (a) a first receptacle containing unused powdered crystals therein and a second receptacle to receive and retain used powdered crystals, used abrasive material and dead skin cells; (b) a suction device; (c) a hand piece comprising a first end having a first opening leading to a suction member located at a second end of the hand piece, the suction member having a central opening, the hand piece further comprising a multiplicity of second openings adjacent its second end, the multiplicity of second openings leading to an internal chamber within the hand piece which internal chamber opens into a second opening at the first end of the hand piece; (d) an abrasive cap made out of exfoliating material, the abrasive cap positioned over and surrounding the suction member, the abrasive cap having a central opening aligned with the central opening of the suction member; (e) means to deliver the unused powdered crystals from the first receptacle to the central opening in the suction member of the hand piece so that once the suction device is turned on, the unused powdered crystals are caused to travel to the hand piece and are expelled out of the central opening in the suction member and the aligned central opening in the abrasive cap; (f) means to return used powdered crystals, used abrasive material and dead skin cells to the second receptacle; (g) whereby, when the suction device is turned on, unused powdered crystals are caused to be expelled from the central opening in the suction member and the aligned central opening in the abrasive cap and onto the surface of the skin while concurrently the abrasive cap is gently rubbed on the skin so that the combination of powdered crystals and abrasive material from the abrasive cap removes dead skin cells and thereafter the used powdered crystals, used abrasive material and dead skin cells are sucked through the multiplicity of second openings adjacent the second end of the hand piece and are caused to travel through the return means to the second receptacle.

Defined more broadly, the present invention is a machine to abrade dead skin cells, comprising: (a) a first means for retaining unused powdered crystals and second means to receive and retain used powdered crystals, used abrasive material and dead skin cells; (b) a delivery and return means; (c) a hand piece comprising a first end having a first opening leading to a hand piece tip located at a second end of the hand piece, the hand piece tip having a central opening, the hand piece further comprising at least one second opening adjacent its second end, the at least one second opening leading to an internal chamber within the hand piece, which internal chamber opens into a second opening at the first end of the hand piece; (d) an abrasive cap made out of exfoliating material, the abrasive cap positioned over and surrounding the hand piece tip, the abrasive cap having a central opening aligned with the central opening of the hand piece tip; (e) means to deliver the unused powdered crystals from the first retaining means to the central opening in the hand piece tip so that once the delivery and return means is activated, the unused powdered crystals are expelled out of the central opening in the hand piece tip and aligned central opening in the abrasive cap; and (f) means to return used powdered crystals, used abrasive material and dead skin cells to the second receiving and retaining means; (g) whereby, when the delivery and return means is activated, unused powdered crystals are caused to be expelled from the central opening in the hand piece tip and the aligned central opening in the abrasive cap and onto the surface of the skin while concurrently the abrasive cap is gently rubbed on the skin so that the combination of powdered crystals and abrasive material from the abrasive cap remove dead skin cells and thereafter, the used powdered crystals, used abrasive material and dead skin cells are sucked through the at least one second opening adjacent the second end of the hand piece and are caused to travel through the return means to the second receiving and retaining means.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A machine to abrade dead skin cells, comprising:
   a. a first receptacle containing unused powdered crystals therein and a second receptacle to receive and retain used powdered crystals, used abrasive material and dead skin cells;
   b. a suction device;
   c. a hand piece comprising a first end having a first opening leading to a suction member located at a second end of the hand piece, the suction member having a central opening, the hand piece further comprising a multiplicity of second openings adjacent its second end, the multiplicity of second openings leading to an internal chamber within the hand piece which internal chamber opens into a second opening at the first end of the hand piece;
   d. an abrasive cap made out of exfoliating material, the abrasive cap positioned over and surrounding the suction member, the abrasive cap having a central opening aligned with the central opening of the suction member;
   e. a first delivery line connecting the first receptacle to said suction device and a second delivery line connecting the suction device to the first opening at the first end of the hand piece, so that once the suction device is turned on, the unused powdered crystals are sucked through the first delivery line and thereafter are caused to travel through the second delivery line to the hand piece; and
   f. a first return line connecting the second receptacle to said suction device and a second return line connecting the suction device to the second opening at the first end of the hand piece;
   g. whereby, when said suction device is turned on, the unused powdered crystals are transmitted from the first receptacle to the first opening at the first end of the hand piece and further caused to travel to the suction member from which the powdered crystals are expelled out of the central opening in the suction member and the aligned central opening in the abrasive cap and onto the surface of skin while concurrently the abrasive cap is gently rubbed on the skin so that the combination of powdered crystals and abrasive material from the abrasive cap removes dead skin cells, and thereafter the used powdered crystals, used abrasive material and dead skin cells are sucked through the multiplicity of second openings adjacent the second end of the hand piece and are sucked through the second return line, the first return line and into the second receptacle.

2. The invention in accordance with claim 1, wherein the abrasive cap is made out of aluminum oxide.

3. The invention in accordance with claim 1, wherein the abrasive cap is made out of metal powder.

4. The invention in accordance with claim 1, wherein the abrasive cap is made out of diamond powder.

5. The invention in accordance with claim 1, wherein the abrasive cap is made out of lava powder.

6. The invention in accordance with claim 1, wherein the abrasive cap is made out of ceramic powder.

7. A machine to abrade dead skin cells, comprising:
   a. a first receptacle containing unused powdered crystals therein and a second receptacle to receive and retain used powdered crystals, used abrasive material and dead skin cells;
   b. a suction device;
   c. a hand piece comprising a first end having a first opening leading to a suction member located at a second end of the hand piece, the suction member having a central opening, the hand piece further comprising a multiplicity of second openings adjacent its second end, the multiplicity of second openings leading to an internal chamber within the hand piece which internal chamber opens into a second opening at the first end of the hand piece;
   d. an abrasive cap made out of exfoliating material, the abrasive cap positioned over and surrounding the suction member, the abrasive cap having a central opening aligned with the central opening of the suction member;
   e. means to deliver the unused powdered crystals from the first receptacle to the central opening in the suction member of the hand piece so that once the suction device is turned on, the unused powdered crystals are caused to travel to the hand piece and are expelled out of the central opening in the suction member and the aligned central opening in the abrasive cap;

f. means to return used powdered crystals, used abrasive material and dead skin cells to said second receptacle;

g. whereby, when said suction device is turned on, unused powdered crystals are caused to be expelled from the central opening in the suction member and the aligned central opening in the abrasive cap and onto the surface of the skin while concurrently the abrasive cap is gently rubbed on the skin so that the combination of powdered crystals and abrasive material from the abrasive cap removes dead skin cells and thereafter the used powdered crystals, used abrasive material and dead skin cells are sucked through the multiplicity of second openings adjacent the second end of the hand piece and are caused to travel through the return means to the second receptacle.

8. The invention in accordance with claim 7, wherein the abrasive cap is made out of aluminum oxide.

9. The invention in accordance with claim 7, wherein the abrasive cap is made out of metal powder.

10. The invention in accordance with claim 7, wherein the abrasive cap is made out of diamond powder.

11. The invention in accordance with claim 7, wherein the abrasive cap is made out of lava powder.

12. The invention in accordance with claim 7, wherein the abrasive cap is made out of ceramic powder.

13. A machine to abrade dead skin cells, comprising:

a. a first means for retaining unused powdered crystals and second means to receive and retain used powdered crystals, used abrasive material and dead skin cells;

b. a delivery and return means;

c. a hand piece comprising a first end having a first opening leading to a hand piece tip located at a second end of the hand piece, the hand piece tip having a central opening, the hand piece further comprising at least one second opening adjacent its second end, the at least one second opening leading to an internal chamber within the hand piece, which internal chamber opens into a second opening at the first end of the hand piece;

d. an abrasive cap made out of exfoliating material, the abrasive cap positioned over and surrounding the hand piece tip, the abrasive cap having a central opening aligned with the central opening of the hand piece tip;

e. means to deliver the unused powdered crystals from the first retaining means to the central opening in the hand piece tip so that once the delivery and return means is activated, the unused powdered crystals are expelled out of the central opening in the hand piece tip and aligned central opening in the abrasive cap; and f. means to return used powdered crystals, used abrasive material and dead skin cells to said second receiving and retaining means;

g. whereby, when said delivery and return means is activated, unused powdered crystals are caused to be expelled from the central opening in the hand piece tip and the aligned central opening in the abrasive cap and onto the surface of the skin while concurrently the abrasive cap is gently rubbed on the skin so that the combination of powdered crystals and abrasive material from the abrasive cap remove dead skin cells and thereafter, the used powdered crystals, used abrasive material and dead skin cells are sucked through the at least one second opening adjacent the second end of the hand piece and are caused to travel through the return means to the second receiving and retaining means.

14. The invention in accordance with claim 13, wherein the abrasive cap is made out of aluminum oxide.

15. The invention in accordance with claim 13, wherein the abrasive cap is made out of metal powder.

16. The invention in accordance with claim 13, wherein the abrasive cap is made out of diamond powder.

17. The invention in accordance with claim 13, wherein the abrasive cap is made out of lava powder.

18. The invention in accordance with claim 13, wherein the abrasive cap is made out of ceramic powder.

* * * * *